United States Patent
Sugo

(10) Patent No.: US 8,329,943 B2
(45) Date of Patent: Dec. 11, 2012

(54) METHOD OF STABILIZING HEME PROTEIN AND STORAGE SOLUTION THEREFOR

(75) Inventor: Shin Sugo, Shimotsuga-gun (JP)

(73) Assignee: Eiken Chemical Co., Ltd., Tokyo (JP)

( * ) Notice: Subject to any disclaimer, the term of this patent is extended or adjusted under 35 U.S.C. 154(b) by 244 days.

(21) Appl. No.: 12/682,412

(22) PCT Filed: Oct. 6, 2008

(86) PCT No.: PCT/JP2008/068182
§ 371 (c)(1),
(2), (4) Date: Apr. 9, 2010

(87) PCT Pub. No.: WO2009/051032
PCT Pub. Date: Apr. 23, 2009

(65) Prior Publication Data
US 2010/0216178 A1    Aug. 26, 2010

(30) Foreign Application Priority Data
Oct. 16, 2007   (JP) ................... 2007-268952

(51) Int. Cl.
*C12Q 1/30* (2006.01)
*C07C 229/24* (2006.01)

(52) U.S. Cl. .............. 562/571; 436/18; 435/27; 435/28; 435/29

(58) Field of Classification Search ............ 435/27, 435/28, 29; 562/571; 436/18
See application file for complete search history.

(56) References Cited

U.S. PATENT DOCUMENTS

| | | | |
|---|---|---|---|
| 5,094,956 A | 3/1992 | Grow et al. | |
| 5,318,726 A | 6/1994 | Rossmaier et al. | |
| 2003/0220522 A1 | 11/2003 | Groth et al. | |
| 2008/0312124 A1* | 12/2008 | Ina ................ | 510/480 |

FOREIGN PATENT DOCUMENTS

| | | |
|---|---|---|
| EP | 0 281 251 A2 | 9/1988 |
| EP | 0 444 263 A1 | 9/1991 |
| EP | 0 708 078 A1 | 4/1996 |
| JP | A-63-243756 | 10/1988 |
| JP | A-63-271160 | 11/1988 |
| JP | A-02-296149 | 12/1990 |
| JP | A-04-145366 | 5/1992 |
| JP | A-05-069466 | 3/1993 |
| JP | A-05-099923 | 4/1993 |
| JP | A-05-281227 | 10/1993 |
| JP | A-05-320109 | 12/1993 |
| JP | A-07-229902 | 8/1995 |
| JP | A-08-012631 | 1/1996 |
| JP | A-09-183773 | 7/1997 |
| JP | A-11-118806 | 4/1999 |
| JP | A-11-218533 | 8/1999 |
| JP | A-2001-249132 | 9/2001 |
| JP | A-2003-014768 | 1/2003 |
| JP | A-2003-194825 | 7/2003 |
| JP | A-2004-035549 | 2/2004 |
| JP | A-2006-335908 | 12/2006 |
| JP | A-2007-145744 | 6/2007 |
| WO | WO 92/02489 A1 | 2/1992 |

OTHER PUBLICATIONS

Supplementary European Search Report in European Patent Application No. 08840474.4; dated Nov. 10, 2010.

* cited by examiner

*Primary Examiner* — Chih-Min Kam
(74) *Attorney, Agent, or Firm* — Oliff & Berridge, PLC

(57) ABSTRACT

A method of stabilizing a hem protein which is effective against the denaturation and degradation of a hem protein typified by hemoglobin and a storage solution therefor. A method of stabilizing a hem protein and a storage solution therefor characterized in that an iminocarboxylic acid or its salt is made to coexist in a sample containing the hem protein, wherein the above-described iminocarboxylic acid is a compound represented by the following general formula (1) wherein R represents a hydrogen atom or a hydroxyl group; and X's represent each a hydrogen atom, an alkali metal or an ammonium group.

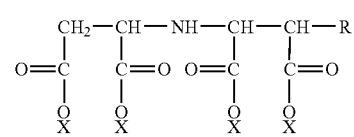

(1)

2 Claims, No Drawings

METHOD OF STABILIZING HEME PROTEIN AND STORAGE SOLUTION THEREFOR

This is a National Phase entry under 35 U.S.C. §371 of International Application No. PCT/JP2008/068182 filed Oct. 6, 2008, which claims the benefit of JP 2007-268952 filed Oct. 16, 2007.

TECHNICAL FIELD

The present invention relates to a method of stabilizing a heme protein, particularly to a method of stabilizing a heme protein in a heme protein test of feces, urine, or a blood sample.

BACKGROUND ART

In recent years, detections of fecal human hemoglobin (fecal occult blood) caused by bleeding from gastrointestinal tracts have been broadly carried out as a screening method of a digestive system disorder, such as colon cancer. The detective method of human hemoglobin is an immunological method employing a specific antibody against human hemoglobin, which takes the place of a related-art dipstick method based on a chemical coloring reaction. This method does not require a dietary restriction, and therefore it becomes established as a convenient testing method.

Examples of an immunological detective method for human hemoglobin include: a single immunodiffusion test in agar plates employing a precipitation line between an anti-human hemoglobin antibody and a human hemoglobin in a testing sample; a latex agglutination test using a latex particle sensitized with an anti-human hemoglobin antibody; enzyme immunoassay or radioimmunoassay, using an anti-human hemoglobin antibody labeled with an enzyme or a radioactive element; and gold colloid aggregation calorimetric method using a gold colloid particle sensitized with an anti-human hemoglobin antibody.

However, in a testing solution, human hemoglobin is gradually denatured, and its antigenicity is decreased. Also, in a testing solution, storage conditions such as storage temperature often accelerates denaturation of human hemoglobin, or bacteria and digestive enzymes in feces often degrade human hemoglobin. Such denaturation and degradation destroy human hemoglobin conformation, resulting in decrease of antigenicity. Therefore, in an immunological method for measuring human hemoglobin, denaturation and degradation of the hemoglobin involve an incorrect diagnosis.

Meanwhile, on a fecal occult blood test, feces are often collected by subjects themselves at their places, and are provided for the test with a closed container, by dissolving the feces in a feces dissolving solution in the container. In such cases, human hemoglobin in feces is often remained in the solution for several days, or placed in a high temperature when utilizing a transportation method such as a postal service. Also, even when feces are collected in a clinical laboratory, it sometime takes longer until carrying out the fecal occult blood test because other tests are also performed. Under such circumstances, an accurate measurement is disturbed by denaturation and degradation of human hemoglobin as described above.

To prevent such denaturation and degradation of human hemoglobin in a solution, a method of adding common antibacterial agents such as thimerosal and chlorhexidine (see Patent Document 1, for example); a method of adding saccharides (see Patent Document 2, for example); addition of hemoglobin of animals other than human (see Patent Document 3, for example); addition of sera of animals other than human (see Patent Document 4, for example); addition of a bacteriolytic enzyme (see Patent Document 5, for example); addition of iron protoporphyrin (see Patent Document 6, for example) and the like have been developed.

However, the techniques for stabilizing human hemoglobin described in those publications cannot fully suppress denaturation and degradation of human hemoglobin in a testing solution containing feces.

Other than those described above, a method of stabilizing hemoglobin using ethylenediaminetetraacetic acid (hereafter, abbreviated as EDTA) have been developed (see Patent Document 7, for example).

However, as a result of replication studies conducted by the inventors of the present invention, it has been confirmed that a sufficient stabilizing action on fecal human hemoglobin cannot be expected with a single use of EDTA.

Then, the applicant of the present invention has been developing a method of adding an aqueous transition metal complex which is more effective for stabilization than EDTA only (see Patent Document 8, for example). Further, the applicant has already developed a method of stabilizing hemoglobin with which a ferrocyanide compound coexists (see Patent Document 9, for example); a method of stabilizing hemoglobin with which an enzymatic degradation product of hemoglobin coexists (see Patent Document 10, for example); a method of stabilizing a heme protein with which transition metals coexist (see Patent Document 11, for example); a method of stabilizing a heme protein with which an organic acid such as malic acid coexists (see Patent Document 12, for example); and a method of stabilizing a heme protein with which a delipidated albumin coexists (see Patent Document 13, for example).

Patent Document 1: Japanese Patent Application Publication No. JP-A-63-271160
Patent Document 2: Japanese Patent Application Publication No. JP-A-63-243756
Patent Document 3: Japanese Patent Application. Publication No. JP-A-2-296149
Patent Document 4: Japanese Patent Application Publication No. JP-A-4-145366
Patent Document 5: Japanese Examined Patent Application Publication No, JP-A-5-69466
Patent Document 6: Japanese Patent Application Publication No. JP-A-5-281227
Patent Document 7: Japanese Patent Application Publication No. JP-A-5-99923
Patent Document 8: Japanese Patent Application Publication No. JP-A-7-229902
Patent Document 9: Japanese Patent Application Publication No. JP-A-11418806
Patent Document 10: Japanese Patent Application Publication No. JP-A-11-218533
Patent Document 11: Japanese Patent Application Publication No. JP-A-2001-249132
Patent Document 12: Japanese Patent Application Publication No. JP-A-2003-014768
Patent Document 13: Japanese Patent Application Publication No. JP-A-2003-194825

DISCLOSURE OF THE INVENTION

Problem to be Solved by the Invention

It is a first object of the present invention to provide a novel method of stabilizing a heme protein, which is effective against denaturation and degradation of a heme protein such as hemoglobin. In particular, the purpose of the invention is to provide a technique for effectively stabilizing hemoglobin which coexists with feces components having strong denaturation and degradation activities.

It is a second object of the present invention to provide a storage solution of a heme protein, which employs a novel stabilizing agent for a heme protein.

It is a third object of the present invention to provide a specific compound for use in a novel method of stabilizing a heme protein.

Means for Solving the Problem

The present invention includes following (1) to (7).
(1) A method of stabilizing a heme protein is characterized by including allowing an iminocarboxylic acid or a salt thereof to coexist in a sample containing the heme protein.
(2) In the method of stabilizing a heme protein according to (1), the iminocarboxylic acid or a salt thereof is a compound of Formula (1);

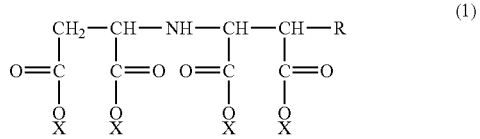

(where R is a hydrogen atom or a hydroxy group, and X is a hydrogen atom, an alkali metal, or an ammonium group), or a mixture thereof.
(3) In the method of stabilizing a heme protein according to (1) or (2), the iminocarboxylic acid or a salt thereof is 3-hydroxy-2,2'-iminodisuccinic acid of Formula (2):

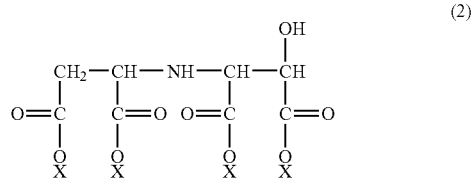

(where X is a hydrogen atom, an alkali metal, or an ammonium group), or a salt thereof.
(4) In the method of stabilizing a heme protein according to any one of (1) to (3), a concentration of the iminocarboxylic acid or a salt thereof falls within a range of 0.001 to 0.200 mol/L.
(5) In the method of stabilizing a home protein according to (1), the heme protein is hemoglobin, myoglobin, peroxidase, or catalase.
(6) In the method of stabilizing a heme protein according to (1), a sample containing the heme protein is feces, urine, or blood.
(7) A storage solution for a heme protein contains the iminocarboxylic acid or a salt thereof according to any one of (1) to (3).
(8) An iminocarboxylic acid or a salt thereof used in the method of stabilizing a heme protein according to any one of (1) to (6).

Effects of the Invention

In the method of stabilizing a heme protein of the present invention, the heme protein can be protected from a biogenic substance having strong denaturation and degradation activities, even under coexistence with a feces component. Accordingly, the method is useful to stabilize hemoglobin which is contained in a sample for analysis of a biogenic substance, for example, for detection of fecal occult blood. Especially, the method contributes to maintain antigenicity of a heme protein, when the heme protein is supposed to be immunologically analyzed and its antigen structure is required to be protected. By the compound used for the method of the present invention, the storage solution, and the method of stabilizing a heme protein, hemoglobin in samples of feces is stabilized effectively, and prevention of a false negative result caused, by denaturation and degradation of hemoglobin can be expected.

BEST MODES FOR CARRYING OUT THE INVENTION

The present invention will be described below in more detail.

In the present invention, the iminocarboxylic acid or a salt thereof is coexisted with a heme protein in a sample. The iminocarboxylic acid can be appropriately selected from ones well known in the art; however, especially the compound of Formula (1) is preferable, and 3-hydroxy-2,2'-iminodisuccinic acid of Formula (2) or a salt thereof is more preferable. Also, examples of an alkali metal of X of Formula (1) and Formula (2), include lithium, sodium, potassium, rubidium, and cesium.

Also, as the iminocarboxylic acid used in the present invention, for example, ones synthesized by a method using aspartic acid and epoxysuccinic acid as raw materials (Japanese Patent Application Publication No. JP-A-9-183773, for example); a method using maleic acid and ammonia as raw materials; a method using aspartic acid and maleic acid as raw materials (Japanese Patent Application Publication No. JP-A-5-320109, for example); a method using maleic acid half ester; maleic acid and ammonia as raw materials (Japanese Patent Application Publication No. JP-A-8-12631, for example) can be used.

A concentration of the iminocarboxylic acid or a salt thereof in a sample containing a heme protein is 0.001 to 0.200 mol/L, more preferably, 0.050 to 0.150 mmol/L. When the concentration of the iminocarboxylic acid or a salt thereof is less than 0.001 mmol/L, an effect of stabilizing a heme protein becomes insufficient. On the other hand, when the concentration of the iminocarboxylic acid or a salt thereof is over 0.200 mmol/L, solubility decreases, and an immunoreaction is also inhibited.

Although it is not essential in the present invention, by adding a known protein protectant as required, an effect to stabilize the heme protein can be further enhanced. Examples of such a protein protectant include an inactive protein such as albumin and gelatin.

Any albumin can be used; however, albumin derived from animal serum or an egg is especially preferable. Specific examples thereof include albumin derived from blood of cattle, horses, goats, sheep, pigs, rabbits, and cubs or fetuses thereof.

In addition to the albumin described in above, an enzymatic degradation product thereof is also known. As albumin of the present invention, a protein induced from such albumin can also be included.

In addition to the above protein protectant, addition of various known protein protective components for a heme protein, such as an antibacterial agent to prevent unnecessary growth of a microorganism, and a buffer giving pH favorable for preserving the heme protein is also effective.

Examples of an antibacterial agent include a series of non-penicillin antibiotics, in addition to bacteriolytic enzyme, ethyl benzoate, penicillin, Fungizone, streptomycin, and cephamycin. Also, it is known that protease inhibitors such as trypsin inhibitor and alpha-2 macroglobulin also stabilizes the heme protein.

A pH of a dispersion medium is adjusted to a range which allows a heme protein to be stably maintained. Under extremely acidic or alkaline conditions, stabilization of the heme protein may be lost, and therefore neutral pH is preferable. Concretely, the pH is 5 to 10, preferably about 6 to 8.

An appropriate buffer can be employed to maintain the pH. For example, the Good's buffer such as hydroxyethylpiperazine-2-ethanesulfonic acid (hereafter, abbreviated as HEPES) and piperazine-bis(2-ethanesulfonic acid) (hereafter, abbreviated as PIPES), gives pH 6 to 8 which may be the most appropriate pH to stabilize a structure of the heme protein. Moreover, the Good's buffer is also utilized as a reaction buffer solution to detect the heme protein by an immune reaction, and it can be listed as an especially preferable buffer. In addition, a phosphate buffer solution, a Tris buffer solution, a glycine buffer solution, a boric acid buffer solution, and the like can also be employed.

The method of stabilizing a heme protein of the present invention can be employed to detect the heme protein in a feces, urine, or blood sample. The heme protein can be appropriately selected from proteins having hem as their components. Examples thereof include hemoglobin, myoglobin, peroxidase, or catalase. Especially, it contributes to maintain antigenicity of a heme protein, when the heme protein is immunologically analyzed and its antigen structure is required to be protected.

The present invention can provide a storage solution for hemoglobin containing an iminocarboxylic acid or salts thereof which act(s) as a stabilization factor of a lime protein.

In addition, the storage solution of the present invention can contain a protein protectant or a buffer as needed. The protein protectant or the buffer can be appropriately selected from the ones listed in the above.

The present invention can provide an immunological measurement method for a heme protein as an application of the stabilizing technique of a heme protein. Examples of the immunological measurement method include a latex agglutination reaction method, a gold colloid aggregation reaction method, immunochromatography, and ELISA. In any measurement methods, antigen activity during storage is maintained by coexistence of an iminocarboxylic acid or salts thereof and a heme protein in a sample, and decrease of measurement value is prevented.

The method of stabilizing a heme protein of the present invention is useful to stabilize heme protein as an analytical object which exists in a biogenic sample. Especially in a heme protein measurement method utilizing an immunological procedure with a heme protein recognition antibody, antigenicity of a heme protein as an analytical object is highly stabilized. Feces, urine, and blood are known as biogenic samples to detect a heme protein. Especially, hemoglobin in feces will be an indicator of bleeding in a gastrointestinal system, and hemoglobin in urine will be an indicator of bleeding in a urinary tract.

When applying the stabilization method of the present invention to hemoglobin in a sample of feces, it is recommended to add an iminocarboxylic acid or salts thereof in a storage solution in which feces are suspended. Usually, in the detection of hemoglobin in feces, the feces are suspended in an appropriate storage solution, and a sample for an immunological analysis will be prepared by filtration as needed.

Hereinafter, the present invention will be described more in detail referring to Examples which should not be construed as limiting the scope of the present invention.

EXAMPLES

Example Hemoglobin Stabilization Effect of HIDS of Different Concentrations

A storage solution was prepared by adding 0 to 0.2 mol/L of tetrasodium 3-hydroxy-2,2'-iminodisuccinate (HIDS) of various concentrations shown in Table 1 to a solution (pH 7.0) containing 0.05 mol/L HEPES, 0.9% sodium chloride, and pure water as remainder. The HIDS manufactured by Nippon Shokubai Co., LTD. was used.

Hemolyzed hemoglobin, or a mixture of hemolyzed hemoglobin and a feces sample was added to the storage solution, and each test solution was measured for a hemoglobin concentration (concentration immediately after addition). Subsequently, the hemoglobin concentration of the test solution stored at 37° C. for 20 hours was divided by the concentration immediately after addition, and residual ratio of hemoglobin was calculated.

A concentration of hemoglobin was measured by OC-SENSOR NEO analyzer (manufactured by Men Chemical Co., Ltd.) using OC Auto III (manufactured by Eiken Chemical Co., Ltd.), which is an immunological measurement reagent for hemoglobin.

As shown in Table 1, in the test solution in which HIDS is added to only hemoglobin, a stabilizing effect was observed by addition of HIDS whose concentration is 0.001 mol/L or more. Also, in the test solution in which hemoglobin and feces are coexisted, the stabilizing effect is observed by addition of HIDS whose concentration is 0.005 mol/L or more. Especially, when a concentration of HIDS added is 0.050 mol/L or more, the effect to stabilize hemoglobin was remarkable.

TABLE 1

Hemoglobin stabilization, effect of HIDS

| Antigen Concentration of HIDS added [mol/L] | Hemoglobin Residual ratio [%] | Hemoglobin + feces sample Residual ratio [%] |
|---|---|---|
| — | 77.7 | 27.5 |
| 0.001 | 82.8 | 28.8 |
| 0.005 | 83.9 | 32.3 |
| 0.010 | 84.2 | 39.2 |
| 0.050 | 84.1 | 50.8 |
| 0.075 | 85.2 | 53.9 |
| 0.100 | 87.8 | 55.9 |
| 0.150 | 88.2 | 57.8 |
| 0.200 | 86.2 | 46.3 |

Comparative Example

An effect to stabilize hemoglobin was examined by a method similar to the method of Example, except for adding ethylenediamine-N,N,N',N'-4 acetic acid (EDTA), iminodiacetic acid (IDA) or N-(2-hydroxyethyl) iminodiacetic acid (HIDA), instead of tetrasodium 3-hydroxy-2,2'-iminodisuccinate (HIDS) of Example.

As shown in Table 2, when EDTA, IDA, or HIDA was used as a chelating agent, a slight stabilizing effect was observed in the test solution of hemoglobin only. However, when IDA or HIDA was used as a chelating agent, any certain stabilizing effect was not observed in the test solution in which hemoglobin and feces are coexisted. When EDTA was used, a slightly higher effect to stabilize hemoglobin was observed even under coexistence of feces, however, when an concentration of HIDS added was 0.010 mol/L or more, the effect to stabilize hemoglobin was much smaller than the effect of the storage solution of Example.

TABLE 2

Hemoglobin stabilization effect of various chelating agents

| Antigen | Hemoglobin Residual ratio [%] | Hemoglobin + feces sample Residual ratio [%] |
|---|---|---|
| No chelating agent added | 77.7 | 27.5 |
| Concentration of EDTA added [mol/L] | | |
| 0.001 | 79.5 | 34.3 |
| 0.010 | 79.8 | 35.8 |
| 0.050 | 82.4 | 37.1 |
| Concentration of IDA added [mol/L] | | |
| 0.001 | 82.1 | 28.0 |
| 0.010 | 80.9 | 27.3 |
| 0.050 | 81.0 | 26.3 |
| Concentration of HIDA added [mol/L] | | |
| 0.001 | 80.3 | 26.1 |
| 0.010 | 79.3 | 26.4 |
| 0.050 | 81.6 | 27.3 |

INDUSTRIAL APPLICABILITY

According to the present invention, when an iminocarboxylic acid or a salt thereof is coexisted with a heme protein in a sample, the heme protein can be maintained stably, and therefor; a false negative caused by denaturation and degradation of hemoglobin can be prevented on a fecal occult blood test. As a result, a fecal occult blood test can be performed more accurately.

The invention claimed is:

1. A method of stabilizing hemoglobin, the method comprising:
adding 3-hydroxy-2,2'-iminodisuccinic acid of Formula (2):

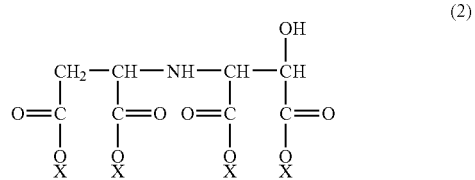

(where X is a hydrogen atom, an alkali metal, or an ammonium group) or a salt thereof at a concentration of 0.010 to 0.200 mol/L to an aqueous solution or feces containing the hemoglobin.

2. A composition comprising hemoglobin stabilized by 3-hydroxy-2,2'-iminodisuccinic acid of Formula (2):

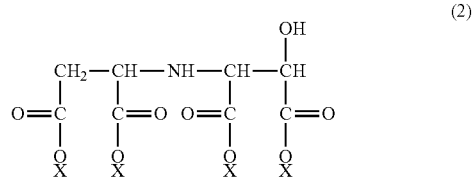

(where X is a hydrogen atom, an alkali metal, or an ammonium group) or a salt thereof.

* * * * *